United States Patent [19]

Suffis et al.

[11] Patent Number: 5,626,852
[45] Date of Patent: May 6, 1997

[54] COMPOSITION CONTAINING BODY ACTIVATED FRAGRANCE FOR CONTACTING THE SKIN AND METHOD OF USE

[75] Inventors: Robert Suffis, Ho-Ho-Kus; Morton L. Barr, East Brunswick, both of N.J.; Kenya Ishida, Yokohama; Kiyohito Sawano, Hiratsuka, both of Japan; Augustinus G. van Loveren, Bedford, N.Y.; Tetsuo Nakatsu, Danville, Calif.; Carter B. Green, Vacaville, Calif.; Gary A. Reitz, Antioch, Calif.; Raphael K. L. Kang, Pleasant Hill, Calif.; Toshiya Sato, deceased, late of Tama-ku, Japan, by Kuniko Sato, administrator

[73] Assignees: The Mennen Company, Morristown, N.J.; Takasago International Corporation, Tokyo, Japan

[21] Appl. No.: 364,927

[22] Filed: Dec. 23, 1994

Related U.S. Application Data

[63] Continuation-in-part of Ser. No. 948,510, Sep. 22, 1992, Pat. No. 5,378,468.

[51] Int. Cl.$^6$ .............................. A61K 7/00; A61K 7/46
[52] U.S. Cl. .................. 424/401; 512/2; 512/27
[58] Field of Search ................ 424/401; 512/2, 512/3, 27

[56] References Cited

U.S. PATENT DOCUMENTS

| | | | |
|---|---|---|---|
| 3,479,297 | 11/1969 | Rutzen | 252/305 |
| 3,751,486 | 8/1973 | Schleppnik | 260/615 |
| 3,922,237 | 11/1975 | Schreiber | 252/522 |
| 3,948,814 | 4/1976 | de Rijke | 512/25 |
| 4,070,397 | 1/1978 | Schmitt | 562/535 |
| 4,107,217 | 8/1978 | Schreiber et al. | 568/384 |
| 4,138,344 | 2/1979 | Choi | 252/1 |
| 4,154,816 | 5/1979 | Roehl et al. | 424/65 |
| 4,346,079 | 8/1982 | Koehl | 424/65 |
| 4,424,146 | 1/1984 | Willis | 252/522 |
| 4,518,582 | 5/1985 | Schamper et al. | 424/66 |
| 4,548,743 | 10/1985 | Sprecker | 252/522 |
| 4,615,830 | 10/1986 | Sprecker | 255/522 |
| 4,720,381 | 1/1988 | Schamper et al. | 424/66 |
| 4,722,835 | 2/1988 | Schamper et al. | 424/66 |
| 4,725,430 | 2/1988 | Schamper et al. | 424/66 |
| 4,891,225 | 1/1990 | Langer | 424/428 |
| 4,927,805 | 5/1990 | Dolfini | 512/27 |

*Primary Examiner*—Sallie M. Gardner
*Attorney, Agent, or Firm*—Antonelli, Terry, Stout & Kraus

[57] ABSTRACT

Described is a fragrancing composition having fragrancing components that are not activated until, e.g., application to the skin of a human. The composition is alkaline or (if anhydrous) capable of producing an alkaline pH when in contact with water, prior to application, and includes (1) a vehicle such that when the composition is in contact with water, prior to application, the composition is at an alkaline pH; and (2) at least one potential fragrance that is at least one compound having little or no odor in the alkaline composition but which, e.g., is hydrolyzed in a lower pH environment to produce compounds having a relatively strong aroma. Upon application of the alkaline composition to the skin surface, the strong buffering capacity of the skin (the surface of which has a normal pH of 5.5–7.0) neutralizes alkalinity of the composition (lowers pH) so as to restore normal skin surface pH; the potential fragrance is then hydrolyzed at the lower pH to release the compound having relatively strong aroma. The potential fragrance can be incorporated as a component of a transparent (clear) deodorant stick composition for application to human axillary regions, the fragrance being released after application to the body.

35 Claims, 2 Drawing Sheets pH6.5, 38°C pH8.6, 38°C

COMPOSITION CONTAINING BODY ACTIVATED FRAGRANCE FOR CONTACTING THE SKIN AND METHOD OF USE

This application is a Continuation-in-Part application of application Ser. No. 07/948,510, now U.S. Pat. No. 5,378,468 filed Sep. 22, 1992, the contents of which are incorporated herein by reference in their entirety.

BACKGROUND OF THE INVENTION

The present invention relates to compositions, particularly compositions for contacting the skin (for example, skin care compositions or personal care compositions), for producing fragrances. More particularly, the present invention relates to such compositions for contacting the skin, wherein the fragrance is formed (e.g., is released from a compound forming a component of the composition) after application of the composition to the skin (that is, body activated fragrances).

It has been desired to provide personal care or skin care products which have components that produce a low level of odor, or are odorless, prior to application to the skin, but which components produce compounds that are pleasant smelling (that is, provides a fragrance) after application to the skin (that is, delayed release of the fragrance). It is desired to provide deodorant or antiperspirant stick products, hand lotions, baby lotions, baby powders, ointments, foot products, facial cleansers, body wipes, facial makeups, colognes, after-shave lotions and/or shaving cream having such components. It is also desired to provide personal care or skin care products (particularly, a deodorant or antiperspirant stick product) that are clear or transparent, and have fragrancing components that, prior to application to the skin (e.g., application to the axillary regions), have a low degree of odor or are odorless, but become pleasant smelling after application.

Solid, transparent, gelled antiperspirant compositions, containing one or more acidic reacting antiperspirant compounds, are known. Note each of U.S. Pat. No. 4,154,816 to Roehl, et al., and U.S. Pat. No. 4,720,381 to Schamper, et al., for example, the contents of each of which are incorporated herein by reference in their entirety. Each of these U.S. patents discloses solid, transparent or clear, antiperspirant gelled stick compositions including an antiperspirant metal compound (such as aluminum chlorohydrate), and alcohols (both monohydric and polyhydric alcohols), with sorbitol dibenzyl ether (DBMSA) utilized as a gelling agent. Such antiperspirant sticks gelled with DBMSA as the gelling agent are utilized as an alkaline or neutral media, but not as an acidic media, since even in the presence of small amounts of water DBMSA hydrolyzes in an acidic medium or will react with a reactive alcohol to form a different acetal. Such antiperspirant stick compositions containing DBMSA as the gelling agent are also known to include conventional fragrances, which begin volatilizing at least as soon as the product is formed.

There are also known antiperspirant sticks consisting largely of gelled alcoholic solutions of antiperspirant compounds, with the gelling agent being a sodium salt of a higher fatty acid, like sodium stearate. However, such sticks cannot contain the usual antiperspirant compounds, because the acidic reaction of these usual antiperspirant compounds causes decomposition of the soap. To avoid this defect, alkaline reacting antiperspirant compounds were developed, like aluminum hydroxy chloride-sodium lactate; but these alkaline reacting antiperspirant compounds suffer from a disadvantage of having a poor antiperspirant effect.

It is also known to delay release of a fragrance from a composition by methods such as micro-encapsulation of the fragrance substance. However, a desired objective of a clear, transparent aqueous-glycol based deodorant stick cannot be obtained using such conventional methods of achieving delayed release of fragrances, including micro-encapsulation. For example, standard methods of micro-encapsulating a fragrance oil in a water-soluble coating system will not work utilizing an aqueous-glycol base, since the water in the deodorant stick base dissolves the protective coating and prematurely releases the fragrance. Thus, water-soluble micro-capsules are not compatible with water/glycol based formulations. Furthermore, a water-insensitive coating or micro-capsule, which is compatible with water/glycol based formulations (such as pH-sensitive or heat-sensitive micro-capsules), is not soluble in the water/glycol formula and must therefore be used as a suspension of the solid, micro-encapsulated fragrance in the liquid formula. As can be appreciated, suspensions of solids in clear liquids result in a formula which loses its transparent properties; suspensions are, at best, translucent, and cannot be absolutely clear.

Perfume compositions containing an acetal compound as the fragrancing substance are known. Thus, U.S. Pat. No. 4,424,146 to Willis, et al. discloses perfume compositions containing acetaldehyde ethyl dihydrolinalyl (6,7-dihydrolinalyl) acetal, the acetal differing from analogous compounds in both odor quality and strength. This patent discloses that addition of the described acetal to various perfume compositions imparts a greener, more lemony and floral character to the original product.

U.S. Pat. No. 3,751,486 to Schleppnik, et al. discloses specific alkyl-substituted unsaturated acetals, useful in preparation and formulation of fragrance compositions such as perfumes and perfumed products due to the pleasing green, floral and woody aromas of the unsaturated acetals. This patent discloses that the acetals described therein have utility in cosmetic, detergent and bar soap formulations.

Neither of U.S. Pat. No. 4,424,146 or No. 3,751,486 discloses that the described compounds can be utilized for delayed release of fragrance, or any mechanism for delayed release of fragrance upon application of, e.g., perfume compositions to the body; and these U.S. Patents do not disclose use of the stated fragrance compounds in clear products (in particular, clear deodorant or antiperspirant stick products).

U.S. Patent No. 3,479,297 to Rutzen, et al. discloses a room deodorant consisting of 60%–80% by weight propellant; 20%–40% by weight solvent and 0.5%–5% by weight active ingredient, the active ingredient being a cyclic acetal or ketal of a monounsaturated aldehyde or ketone having at least 3 carbon atoms and an aliphatic alcohol, the aliphatic alcohol being a 1,2-diol or 1,3-diol having 8–24 carbon atoms. This patent discloses that the cyclic acetal or ketal active ingredient is essentially odorless, but reacts within short periods of time with odiferous substances present in a room to form complexes neutral in odor, the active ingredients being sufficiently stable to retain their effectiveness over a comparatively long period of time.

U.S. Pat. No. 3,479,297 discloses room deodorants (not body and/or underarm deodorants or other personal care or skin care compositions) containing specific acetals or ketals which react with noxious substances. Such disclosure does not describe compounds which are odorless or of a low level of odor when applied (e.g., when applied to skin) and which are converted into pleasant smelling substances after application.

Accordingly, it is still desired to provide compositions (e.g., personal care or skin care products) having a delayed release of fragrance, especially a clear stick deodorant or antiperspirant product containing components for providing a fragrance, so as to achieve a delayed release of fragrance. It is particularly desired to provide such product wherein the fragrance is released after contact of the composition with skin (that is, a body activated fragrance).

SUMMARY OF THE INVENTION

Accordingly, it is an object of the invention to provide a composition (e.g., a personal care product (such as a deodorant or antiperspirant for axillary use or other personal care product), or skin care product, to contact the skin), having delayed release of fragrance (release of fragrance after application of the composition), and method of using such composition.

It is a further object of the present invention to provide a personal care or skin care product having delayed release of fragrance, wherein the release of fragrance does not occur until after contact with the skin (that is, wherein the fragrance is activated by the skin), and method of using such product.

It is a still further object of the present invention to provide a personal care product or skin care product, in the form of a solution, powder, lotion, cream or other emulsion, or gelled stick (useful in, for example, underarm deodorants or antiperspirants or other deodorants contacting the body, or in hand lotions, baby powders, baby lotions, ointments, foot products, facial cleansers, body wipes, facial make-up, colognes, after-shave lotions and shaving creams), having at least one fragrancing component that is odorless or of a low level of odor prior to application to the human skin, but which changes into a pleasant smelling substance (that is, which changes into a compound having a strong aroma) when in contact with the human skin.

It is a still further object of the present invention to provide a personal care or skin care product, including a vehicle such that the product is useful in liquid roll-ons, sprays, aerosols and cream products applied to the human skin, having at least one fragrancing component that is odorless or of a low level of odor when applied, but which changes into a pleasant smelling substance when in contact with the skin.

It is a still further object of the present invention to provide a transparent (e.g., clear) deodorant or antiperspirant stick product with a delayed release of fragrance, the substance providing the fragrance being odorless or of a low level of odor prior to application but which changes into a pleasant smelling substance in contact with the human skin.

The present invention is in part based upon the recognition by applicants that human skin exhibits a "buffer capacity" which vigorously maintains a constant pH value. This buffer capacity is referred to as "the acid mantle". Human skin acts rapidly to neutralize acidic or alkaline insults outside this constant pH value.

Application of a high pH soap to the skin is an example of an alkaline insult. A soap-based deodorant stick, which independently exhibits a pH of 9.5–10, is almost immediately neutralized after application to the skin by the "acid mantle" of the skin, to a pH of 8.2–8.3. Within seven hours of application, underarm (axillary) skin pH at the site of application is virtually restored to its original value of pH=5.5–7.0, due to the aforementioned buffer capacity of the skin.

Utilizing this recognition of the "buffer capacity" of the skin, applicants incorporate in a skin contact composition at least one component ("potential fragrance") which maintains its integrity at a pH above about 8.0 and which does not release fragrance at this alkaline pH, but which begins to lose its integrity as the pH lowers to a pH of 8.0 or below and releases fragrance as skin pH returns to a normal, original (prior to application of the composition) value. Desirably, the potential fragrance retains its integrity (does not release fragrance) at a pH above 7.5, but begins to lose its integrity at a pH of 7.5 and below to release fragrance.

Thus, applicants incorporate, in their skin care product, various components (molecules) which are chemically stable and practically odorless in an environment having a pH of 9.5–10 (for example, the environment of the aqueous/glycol soap-based deodorant stick), but which begin to hydrolyze at a pH of 8 and below (desirably, at a pH of 7.5 and below) to release the odorous portion of the molecule. Therefore, in a, e.g., deodorant base of pH=9.5–10, the component is a "potential fragrance", capable of forming a compound having a pleasant scent (e.g., upon lowering of the pH), yet itself being stable and relatively odorless. Upon application to the skin, as the pH of the environment of the component lowers to a pH of 8 or less (desirably a pH of 7.5 or less), and as the skin pH lowers towards 5.5–7.0, fragrance is released due to hydrolysis of the molecule releasing the odorous portion of the molecule; and as the skin pH lowers towards 5.5–7.0, more and more fragrance is released (e.g., over a roughly 7–12 hour period).

Accordingly, the present invention provides a composition, and method of using such composition, having a potential fragrance, the potential fragrance only being activated after application of the composition to, e.g., the skin. The composition is an alkaline composition (e.g., has a pH of 7.5 or greater, such as 8.0 or greater). The composition includes a vehicle so that the composition can be applied, and at least one potential fragrance. The at least one potential fragrance has little or no odor, and is stable in the alkaline composition (e.g., in an alkaline solution including water). However, upon lowering the pH of the environment of the potential fragrance, the potential fragrance reacts (e.g., is hydrolyzed) to release an odorous portion of the potential fragrance, thereby providing a fragrance (e.g., a relatively strong, pleasant smelling aroma).

More specifically, the present invention provides a composition for contacting human skin, having a body activated fragrance that is odorless or of a low level of odor when applied to the skin (e.g., applied to the skin in an alkaline vehicle, having a pH greater than 7.5) and which is converted by natural skin pH changes (due to the buffer capacity of the skin) into a pleasant smelling substance, e.g., by hydrolysis of the compound to release the odorous portion of the molecule, and method of using such composition.

Various specific materials which are stable at alkaline pH (e.g., greater than pH=7.5), yet which undergo hydrolysis at a more acidic pH range (e.g., at most pH=7.5) to produce pleasant odors, can be incorporated in the composition of the present invention. Specifically, and illustratively (without limitation), acetals or ketals, e.g., of carbonyl compounds, which are stable with respect to hydrolysis at alkaline pH (e.g., greater than pH=8.0; preferably, greater than pH=7.5), yet which undergo hydrolysis at a more acidic pH range and which produce pleasant odors upon hydrolysis, are useful as the potential fragrances or body activated fragrances of the composition of the present invention. Hereinafter, by acetals or ketals, useful in the present invention, we mean acetals, or ketals, of fragrance materials which exhibit the desired pH-dependent hydrolysis behavior and resultant odor (e.g., pleasant aroma) after hydrolysis. The composition can be applied to the skin, using a suitable vehicle, and can achieve delayed release of fragrance (after application to the skin).

Another class of compounds useful as potential fragrances in the present invention are orthoesters. These orthoester compounds generally have the formula:

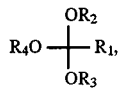

where at least one of $R_1$, $R_2$, $R_3$ and $R_4$ is capable of forming a material having a fragrance upon hydrolysis of the orthoester. More specifically, (and illustratively, while not limiting), $R_1$ can be H, $CH_3$, phenethyl, cinnamyl, phenylpropyl, benzyl, santalyl, etc.; and $R_2$, $R_3$ and $R_4$ can be identical to each other or different, and can be $CH_3$, phenethyl, cinnamyl, phenylpropyl, benzyl, santalyl, etc. ($R_2$, $R_3$ and $R_4$ cannot be H); however, if $R_1$ is $CH_3$ or H, then $R_2$, $R_3$ and $R_4$ cannot all be $CH_3$ (that is, at least one of $R_1$–$R_4$ must be phenethyl, cinnamyl, phenylpropyl, etc., i.e., a radical that forms a material with a fragrance upon hydrolysis). Thus, at least one of $R_1$–$R_4$ must be a radical that forms a material with a fragrance upon hydrolysis.

The compounds as described in the foregoing can be utilized in the various personal care and skin care products as discussed in the foregoing, in the form of a solution, lotion, cream or other emulsion, gelled stick, aerosol, spray or liquid roll-on; and, in particular, can be utilized to provide delayed release of fragrance in a transparent (clear) deodorant or antiperspirant stick product.

The composition of the present invention is an alkaline composition, or, if non-aqueous, is capable of providing an alkaline composition in contact with water. Hereinafter, when we refer to a composition capable of providing an alkaline composition when in contact with water, we mean both (1) an alkaline composition (e.g., an alkaline composition containing water) and (2) a composition which will be alkaline in contact with water (e.g., an anhydrous composition but which will be alkaline in contact with water). The compositions of the present invention are not acidic. In acidic compositions, the potential fragrance would hydrolyze, releasing fragrance prior to application.

As is clear from the prior paragraph, the present invention does not require a water-based (or even water-containing) composition. For example, various powder compositions and gelled stick compositions fall within the present invention. Powders (e.g., baby powder, talcum powder) can be, for example, non-aqueous. Certain gelled sticks (e.g., stearyl alcohol-cyclomethicone (Dow Corning Corp.)) are also non-aqueous. Moreover, compositions according to the present invention (e.g., clear or transparent compositions, such as clear or transparent stick compositions) can contain relatively small amounts of water, e.g., about 5% by weight. Such clear or transparent compositions containing 5% by weight water are illustrative, and such compositions can contain more or less than 5% by weight of water.

Since the composition according to the present invention is to be alkaline (or, if, e.g., non-aqueous, alkaline in contact with water or water-containing substances), there is a need to ensure the presence of water-soluble, alkaline pH producing ingredients in any composition containing any amount of water (or which will come into contact with any amount of water prior to application). In this regard, a composition which contains as little as 0.5% by weight water can cause some degree of hydrolysis, especially if other polar solvents such as ethanol or propylene glycol are present. Such water-soluble, alkaline pH producing ingredients, commonly used in the art, include sodium bicarbonate, calcium or magnesium hydroxide, calcium or magnesium oxide, alkaline earth and alkali metal silicates, alkanolamines, tris (hydroxymethyl) aminomethane (TRIS buffer), sodium hydroxide, etc. Such water-soluble, alkaline pH producing ingredients can be used for either aqueous (water-containing) or non-aqueous compositions; however, for non-aqueous compositions, powders such as sodium bicarbonate, magnesium oxide, etc., are preferred.

The presently described potential fragrances can be used in non-acidic antiperspirant compositions, with antiperspirants that are alkaline in nature (e.g., sodium aluminum lactate). However, presently used antiperspirant compositions include antiperspirants that are acidic in nature (e.g., aluminum chlorohydrate); the potential fragrance, if used in such presently used antiperspirant compositions containing acidic antiperspirants, will not attain the objective of delayed release of fragrance upon contact with, e.g., sweat.

In summary, according to one aspect of the present invention a "potential fragrance", which exhibits little or no odor when present in an alkaline composition, and is applied to human skin in an alkaline composition (or in a composition capable of producing an alkaline pH when in contact with water), hydrolyzes on human skin as the skin pH is naturally lowered following alkaline insult due to application of the alkaline material to the skin. The resulting hydrolysis product, which is odorous, imparts a pleasant smell to the skin. Again, the basis for the hydrolyzing of the potential fragrance is the strong buffer capacity of the human skin to maintain a skin surface pH in the acidic range of 5.5–7.0, depending upon skin and population, the skin buffer capacity neutralizing the alkalinity caused by the application of alkaline material to the skin and restoring normal pH (to thereby cause the hydrolysis).

Typically, several different potential fragrances (for example, several different carbonyl acetals or ketals) are compounded together into the alkaline formulation, to be applied to the skin, to ensure formulation of desirable "fragrances" or odors following hydrolysis on the skin.

In a further aspect of the present invention, sodium stearate-based deodorant sticks containing water, propylene glycol, monohydric alcohols, optionally other fragrances and colors, and including potential fragrances as discussed previously (including, specifically, orthoesters, and/or acetals or ketals of carbonyl compounds as discussed above) can be provided to achieve delayed release of fragrance after application to the skin, while still maintaining a transparent or clear deodorant product.

Accordingly, by the present invention a product can be provided having delayed release of fragrance (e.g., a fragrancing product for contact with human skin, such as a personal care or skin care product, can be provided having delayed release of fragrance, delayed until after contact with the human skin; that is, a body activated fragrance), without the need of standard techniques for delayed release including, e.g., micro-encapsulation; moreover, the present invention enables formation of a transparent (clear) deodorant or antiperspirant stick product having delayed release of fragrance.

DETAILED DESCRIPTION OF THE INVENTION

Figure 1:
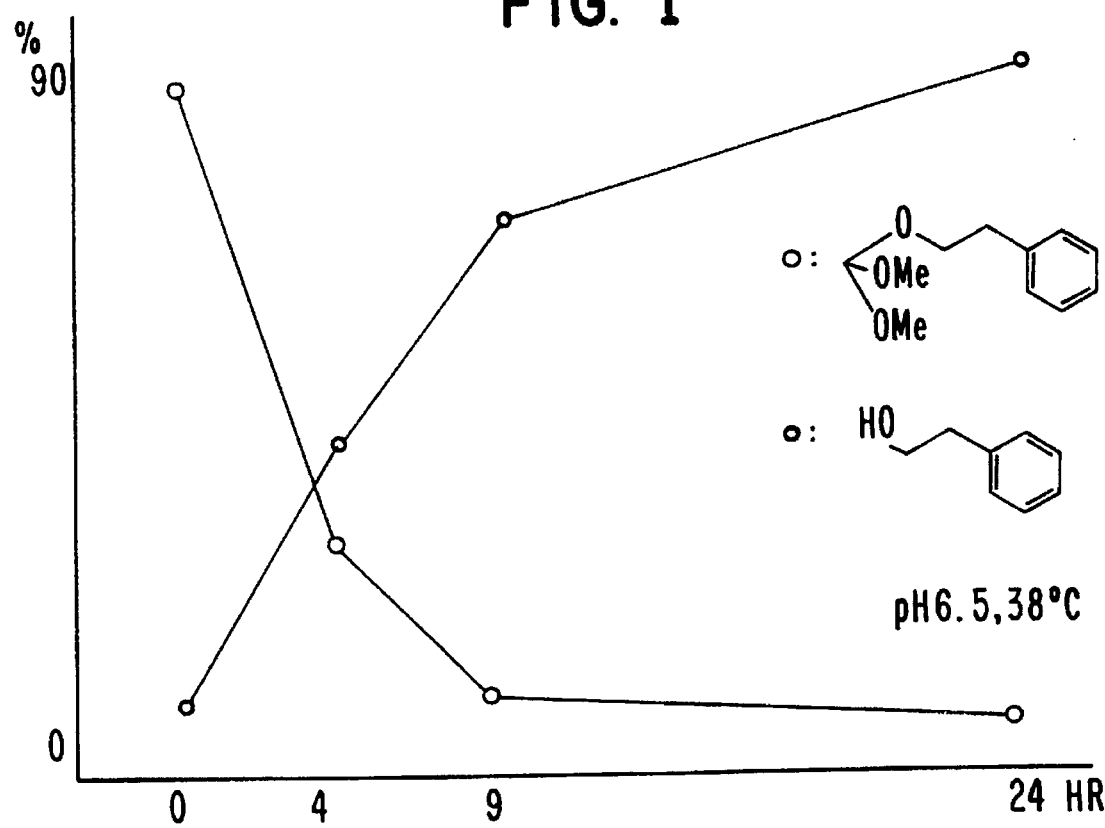
FIGS. 1 and 2 demonstrate the pH-dependent hydrolysis of a specific orthoester.

While the invention will be described in connection with specific and preferred embodiments, it will be understood that it is not intended to limit the invention to those embodiments. On the contrary, it is intended to cover all alterations, modifications and equivalents as may be included within the spirit and scope of the invention as defined by the appended claims.

Throughout the present description, where it is disclosed that the composition and method include or comprise specific materials or steps, it is also within the contemplation of the present invention that the composition or method consists essentially of, or consists of, the recited materials or steps.

The present invention contemplates a composition for delayed release of fragrance; and in particular, a composition for application to the skin of a human (for example, a personal care product or skin care product), having potential fragrance components that are odorless or of a low level of odor prior to application, but which change into a pleasant smelling substance after contact with the skin (in particular, having a body activated release of fragrance). The composition is alkaline when in contact with or containing water, and includes a vehicle and at least one potential fragrance component (in addition to any other fragrance components and/or other components such as coloring), the potential fragrance component being odorless or of a low level of odor in alkaline conditions (an environment of pH of, for example, 9.5–10), yet which hydrolyzes at lower pH to produce the pleasant smelling substance. The decrease in pH is achieved upon contact with the skin, which due to the skin's buffer capacity will neutralize the alkaline composition to provide an environment for the potential fragrance component that will cause hydrolysis of the potential fragrance to produce the pleasant smelling substance.

As indicated previously, various acetals or ketals, e.g., acetals or ketals of carbonyl compounds, which are stable with respect to hydrolysis at alkaline pH (e.g., pH of greater than 8.0, preferably, pH greater than 7.5) but which undergo hydrolysis at a more acidic pH, and which produce pleasant odors upon hydrolysis, are useful as the potential fragrances or body activated fragrances incorporated in the compositions of the present invention. Specific compounds useful as potential fragrances according to the present invention are listed in the following as Formulae I–IV.

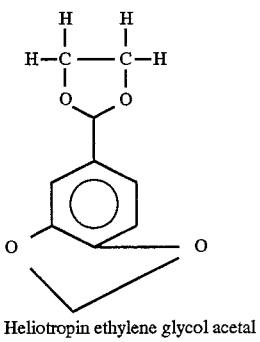

Heliotropin ethylene glycol acetal

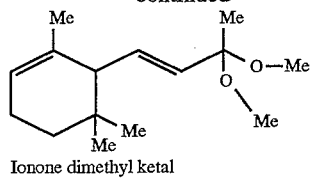

Ionone dimethyl ketal

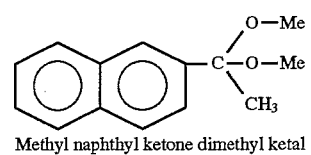

Methyl naphthyl ketone dimethyl ketal

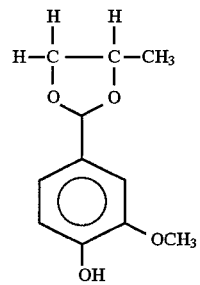

Vanillin propylene glycol acetal

Other such acetals or ketals that are hydrolyzable under more acidic conditions to form an odoriferous compound, but which are stable and have little or no odor under more alkaline conditions, include (illustratively) citral butanetriol acetal, α-amyl cinnamaldehyde dimethyl acetal, and α-amyl cinnamaldehyde butanetriol acetal.

Generally, the acetals and ketals that can be used according to the present invention include (but are not limited to) heliotropine polyol acetal, ionone dialkyl ketal, methyl naphthyl ketone dialkyl ketal, citral polyol acetal, α-amyl cinnamaldehyde dialkyl acetal, α-amyl cinnamaldehyde polyol acetal, vanillin dialkyl acetal, vanillin alkylene acetal, anisic aldehyde dialkyl acetal, anisic aldehyde polyol acetal, citral dialkyl acetal, and vanillin polyol acetal. Specific compounds within the scope of these acetals and ketals include ionone dimethyl ketal, ionone diethyl ketal, methyl naphthyl ketone dimethyl ketal, methyl naphthyl ketone diethyl ketal, citral ethylene glycol acetal, citral butanediol acetal, citral butanetriol acetal, citral propylene glycol acetal, α-amyl cinnamaldehyde dimethyl acetal, α-amyl cinnamaldehyde diethyl acetal, α-amyl cinnamaldehyde propylene glycol acetal, α-amyl cinnamaldehyde butanetriol acetal, α-amyl cinnamaldehyde ethylene glycol acetal, vanillin dimethyl acetal, vanillin diethyl acetal, vanillin ethylene acetal, vanillin propylene acetal anisic aldehyde dimethyl acetal, anisic aldehyde diethyl acetal, anisic aldehyde propylene glycol acetal, anisic aldehyde butanetriol acetal, anisic aldehyde ethylene glycol acetal, citral dimethyl acetal, citral diethyl acetal, and vanillin propylene glycol acetal.

Illustratively, the acetals and ketals can be synthesized by a technique which is a modification of the methods described in Organic Syntheses Collective Volume 3, pages 731–732. An example of this technique is shown in the following. Of course, such technique is illustrative and not limiting.

A mixture of beta-methyl naphthyl ketone (200 g), trimethyl orthoformate (430 g) and toluene (250 ml) were stirred under nitrogen atmosphere for 10 min. To this mixture, 1.8 ml of (47%) $BF_3OEt_2$ was added and stirred for 48 hours at room temperature, washed with aqueous $NaHCO_3$ and saturated NaCl solution. The mixture was then dried over $Na_2SO_4$, concentrated and distilled under reduced pressure to give 192 g of beta-methylnaphthylketone dimethyl ketal.

b.p. 113°–116° C./1.5mmHg

NMR($CDCl_3$): 1.62(3H,s), 3.25(6H,s), 7.4–8.1(7H,m)

IR(neat): 3055, 1680, 1280

MS m/z: 184($M^+$-MeOH)

Also, shown in the following are illustrations of the hydrolysis reactions which take place under acidic conditions, to release the pleasant smelling substances from the potential fragrances. The specific formulae for the following are the four above-listed compounds I–IV.

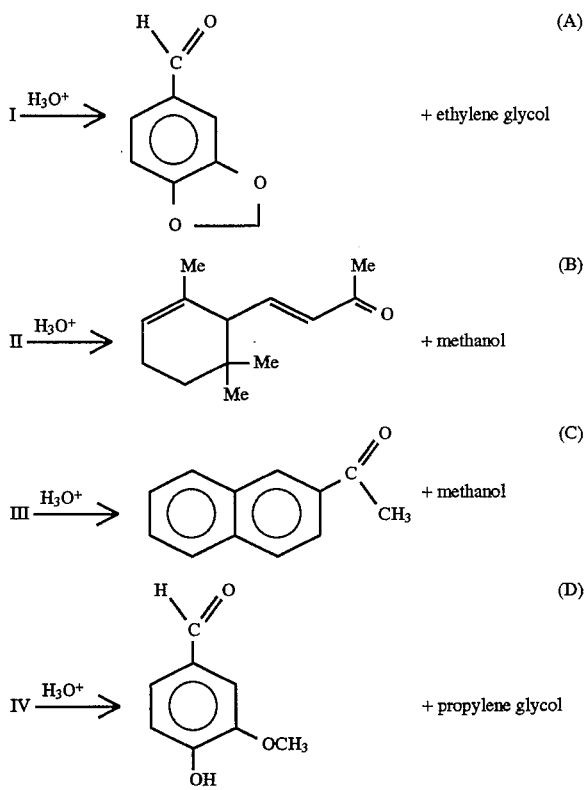

The foregoing compounds and reactions are merely illustrative of various acetal and ketal compounds, and fragrance materials formed therefrom, which can be utilized according to the present invention. In general, the acetals and/or ketals can be selected based upon the fragrances desired, and upon the following considerations to obtain a long-lasting fragrance. Thus, acyclic acetals hydrolyze faster than cyclic acetals. Acetals hydrolyze more quickly than ketals. Acetals formed from short-chain alcohols hydrolyze faster than acetals formed from longer-chain alcohols. Dimethyl acetals (DMA), diethyl acetals (DEA) and propylene glycol acetals (PGA) generally hydrolyze quickly at a pH of 6 (within the range of normal pH values of the skin); larger acetals will also hydrolyze, but more slowly and at lower pH. Allylic conjugation with the hydrolysis site results in faster hydrolysis than non-conjugation. Electron-donating substituents on an aromatic ring with the hydrolysis site increase the rate of hydrolysis. And electron-donating groups at the alpha position of an olefin conjugated to the hydrolysis site decrease the rate of hydrolysis.

Not only can such acetals or ketals (e.g., acetals or ketals of carbonyl compounds, such as acetals or ketals of conjugated carbonyl compounds) be utilized, but also other compounds, including (but not limited to) esters, amides and hydrolyzable derivatives of carbonyl compounds, capable of producing pleasant odors, can be utilized according to the present invention.

As mentioned previously, another class of compounds useful as potential fragrances in the present invention are orthoesters, generally represented by the formula

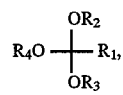

where at least one of $R_1$–$R_4$ forms a fragrance material upon hydrolysis of the orthoester. More specific definitions of $R_1$–$R_4$ have previously been given.

In the following is set forth illustrative types of orthoester compounds for use in the present invention. These orthoester compounds are illustrative and not limiting, and show (particularly with the aforementioned acetals and ketals, esters, amides, etc.) the wide range of potential fragrances which can be used as part of the present invention. In the illustrative types of orthoesters in the following, $R_1$–$R_4$ refer to the $R_1$–$R_4$ of the formula for orthoesters in the immediately preceding paragraph.

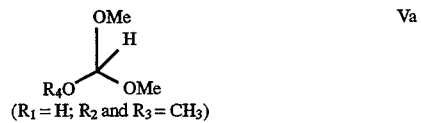

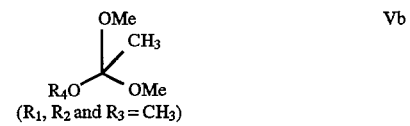

where $R_4$ can be phenethyl, cinnamyl, phenylpropyl, benzyl, geranyl, citronellyl, C-3-hexenyl and santalyl;

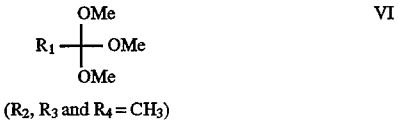

where $R_1$ can be phenyl, cinnamyl or benzyl;

where $R_2$–$R_4$ can be the same or different, and can be phenethyl, cinnamyl, phenylpropyl, benzyl, geranyl, citronellyl, C-3-hexenyl, and santalyl (the same moieties for R as in the formulae Va and Vb).

The orthoesters can be synthesized by techniques known to those skilled in the art. Illustratively, an example of such techniques is shown in the following. Of course, such technique is illustrative and not limiting.

Synthesis of triethyl orthophenylacetate

To a mixture of dry ethanol (20 g) and dry chloroform (15 ml), 50 g of benzylnitrile was added and stirred at 10°–15° C. To this mixture, dry hydrochloride (15.6 g) was introduced. After 48 hours at room temperature, dry ethanol (100 ml) was added, and then left at room temperature for 2 days. The mixture was poured into a 5% NaOH solution. Then extraction was performed with chloroform and concentrated to give an oil (43 g). Triethyl orthophenylacetate was refined by distillation. (b.p 69°–71° C./1.5 mmHg, NMR(δ) 1.1–1.3 (9H,m), 3.1(2H,s), 3.5–3.6(6H,m), 7.2–7.4(5H,m)).

Also, shown in the following (E) and (F) are illustrations of the hydrolysis reactions which take place under acidic conditions, to release the pleasant smelling substances from the orthoester potential fragrances. The specific formulae for the following are the above-described compounds Va, Vb, VI and VII. Also described in the following are the fragrance materials formed, for a given $R_4$.

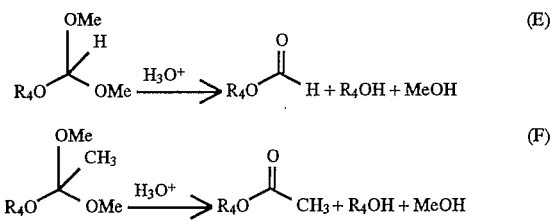

Acid-hydrolyzed products of (E) and (F) are shown in the following Table A.

TABLE A

| Identity of $R_4$ in starting material | Hydrolysis Products |
| --- | --- |
| Phenethyl | Rose P, Rose P acetate (formate) |
| Cinnamyl | Cinnamic alcohol, Cinnamyl acetate (formate) |
| Phenylpropyl | Phenylpropyl alcohol<br>Phenylpropyl acetate (formate) |
| Benzyl | Benzyl alcohol, Benzyl acetate (formate) |
| Geranyl | Geraniol, Geranyl acetate (formate) |
| Citronellyl | Citronellol, Citronellyl acetate (formate) |
| c-3-Hexenyl | c-3-Hexenol, c-3-Hexenyl acetate (formate) |
| Santalyl | Santalol, Santalyl acetate (formate) |

(G) $R_I\!-\!\!\overset{\displaystyle OMe}{\underset{\displaystyle OMe}{|}}\!\!-\!OMe \xrightarrow{H_3O^+} R_I\!-\!\overset{O}{\overset{\|}{C}}\!-\!OMe + 2MeOH$ Acid-hydrolyzed products of (G) are shown in the following Table B.

TABLE B

| Identity of $R_1$ in starting material | Hydrolysis Products |
| --- | --- |
| Phenyl | Methyl benzoate |
| Cinnamyl | Methyl cinnamate |
| Benzyl | Methyl phenylacetate |

(H) $CH_3\!-\!\!\overset{\displaystyle OR}{\underset{\displaystyle OR}{|}}\!\!-\!OR \xrightarrow{H_3O^+} CH_3\!-\!\overset{O}{\overset{\|}{C}}\!-\!OR + CH_3\!-\!\overset{O}{\overset{\|}{C}}\!-\!OR + ROH$ R is the same as $R_2$, $R_3$ and $R_4$ of Formula VII. Each R can be the same or different, and can be of any of the starting materials listed for "$R_4$" in Table A.

Figure 2:
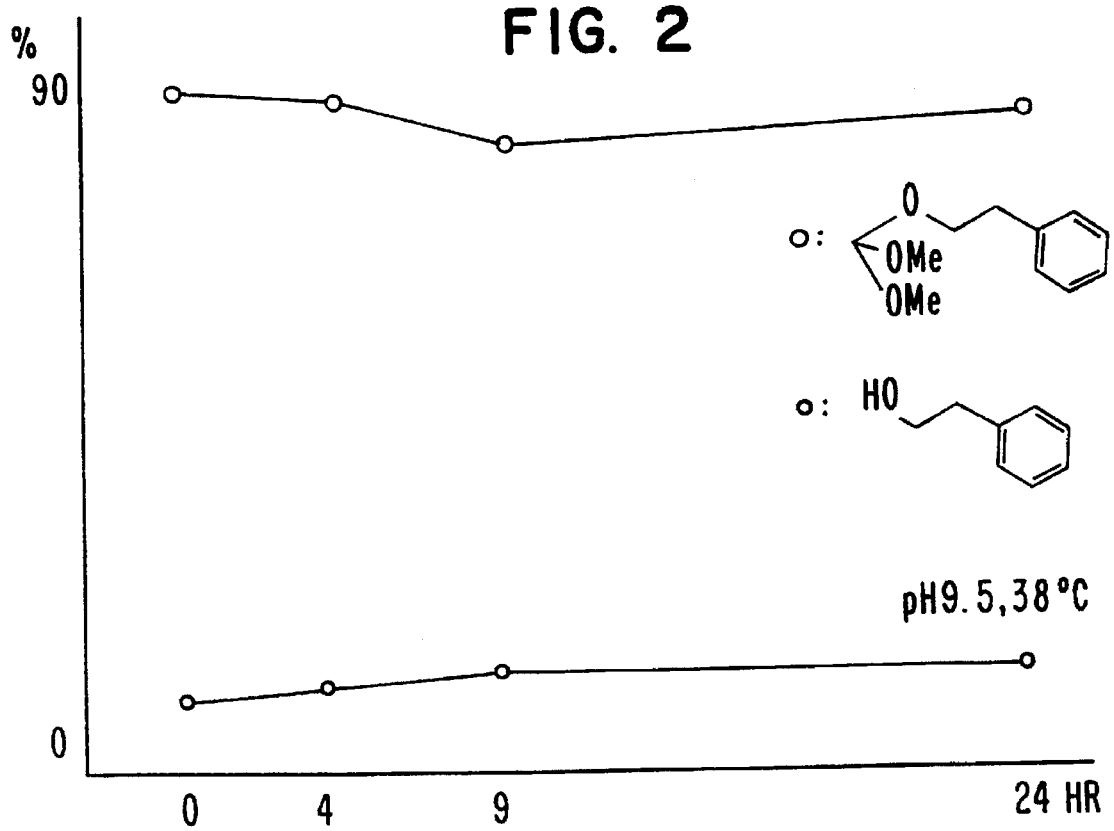

FIGS. 1 and 2 demonstrate the pH-dependent hydrolysis of a specific orthoester, where (in the general formula for orthoesters) $R_1$=H, $R_2$=phenethyl, and $R_3$=$R_4$=$CH_3$. FIG. 2 shows that at pH=9.5, the concentration of the specific orthoester, representing 90% of the contents of a reaction mixture, is unchanged over a 24-hour period while the hydrolysis product, phenethyl alcohol, is unchanged over a 24-hour period at close to 0% of the reaction mixture. On the other hand, FIG. 1 shows that at pH=6.5, the orthoester hydrolyzes rapidly and in about 9 hours has essentially disappeared from the reaction mixture. The fragrance material phenethyl alcohol has increased in concentration to completely replace the starting material. Thus, FIGS. 1 and 2 demonstrate use of a specific orthoester as a potential fragrance, whereby at lower pH a material providing a fragrance is released from the orthoester.

Figure 3:
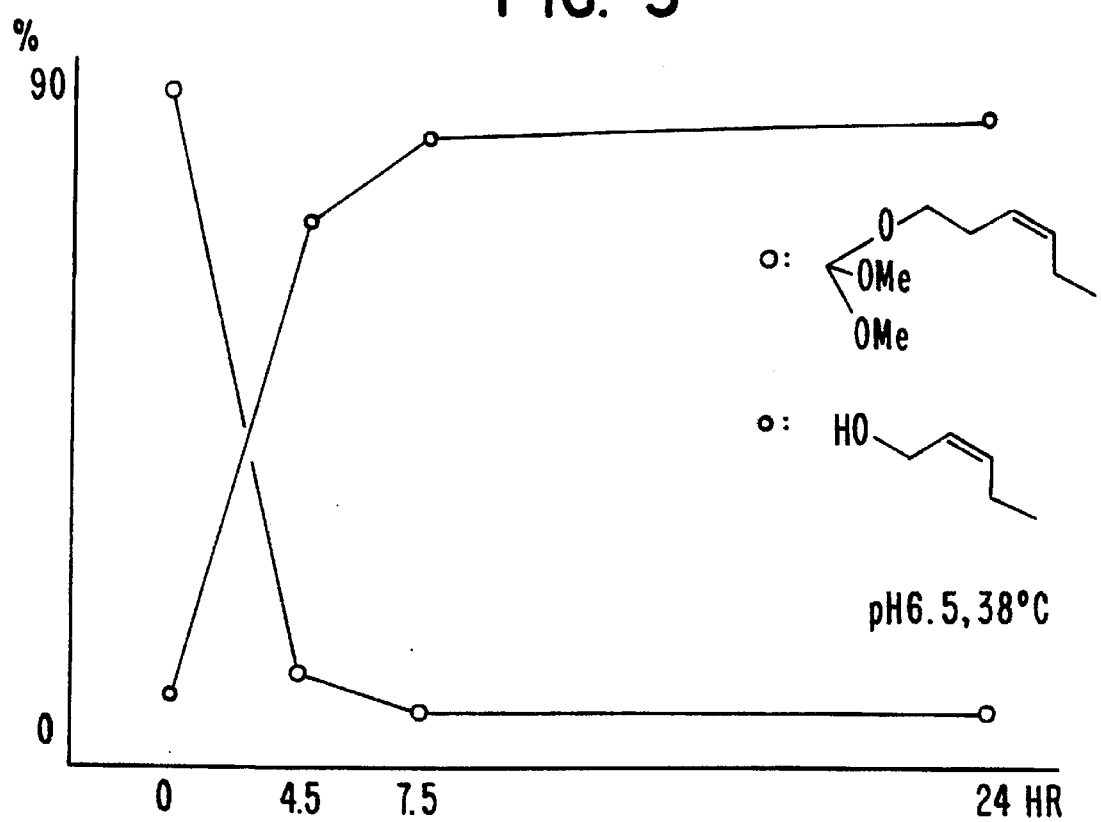
FIGS. 3 and 4 demonstrate the pH-dependent hydrolysis of another specific orthoester.
Figure 4:
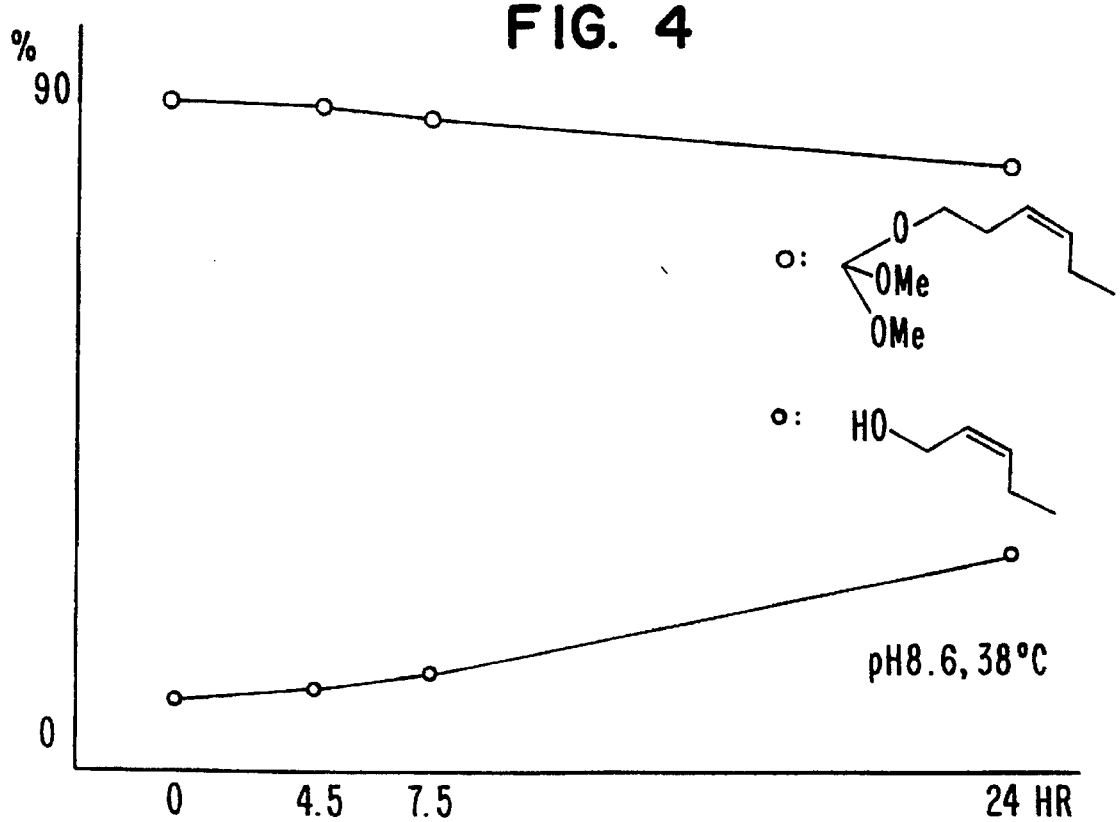

FIGS. 3 and 4 demonstrate the pH-dependent hydrolysis of dimethyl cis-3-hexenyl orthoformate, where (in the general formula for orthoesters) $R_1$=H, $R_2$=cis-3-hexenyl, and $R_3$=$R_4$=$CH_3$. FIG. 4 shows that, at pH=8.6, and from a reaction mixture wherein the orthoester represents 70–80% of the mixture, only a small percentage of the orthoester hydrolyzes over a 24-hour period, while the hydrolysis product, cis-3-hexenol, represents 0.–35% of the mixture after 24 hours. At a pH of 9 or higher, the concentration of hydrolysis product is unchanged over a 24-hour period, at close to 0% of the reaction mixture. On the other hand, FIG. 3 shows that at pH=6.5, the orthoester hydrolyzes rapidly and in about 7 hours has essentially disappeared from the reaction mixture. Thus, FIGS. 3 and 4 demonstrate use of a different orthoester, than the orthoester used in connection with FIGS. 1 and 2, as a potential fragrance, whereby at lower pH a material providing a fragrance is released from the orthoester.

Various compositions, for contact with the skin, fall within the scope of the present invention, including various skin care and personal care products. Based upon the specific vehicle utilized, the compositions are useful as liquid roll-on compositions, powders, spray compositions, aerosol compositions, stick compositions and cream compositions, applied to the human skin. For example, the compositions according to the present invention, utilizing a vehicle known in the art, and possibly other components, including, e.g., water, to form an alkaline composition, can be used for underarm deodorants, hand lotions, baby powder, baby lotions, ointments, foot products, facial cleansers, body wipes, facial make-up, colognes, after-shave lotions and shaving creams.

Apart from the incorporation of the potential fragrance as discussed in the foregoing, and the necessity of an alkaline environment (e.g., an alkaline vehicle) or an environment which becomes alkaline when in contact with water, the compositions according to the present invention can include conventional components which are used in conventional compositions, e.g., for liquid roll-ons, sprays, aerosols, creams and stick products. Thus, conventional components of various skin care and personal care products (e.g., stick deodorants, baby powders, hand lotions, baby lotions, etc.) can also be incorporated within the compositions according to the present invention, as long as such components do not so affect composition pH such that hydrolysis of the potential fragrance occurs, and as long as such components are inert to the potential fragrance (or as long as such components do not prevent the potential fragrance from releasing the pleasant smelling substance by, e.g., hydrolysis after application of the composition to the skin).

Of course, the compositions according to the present invention can include conventional fragrances, as long as such fragrances are inert to the potential fragrances of the present invention and do not so affect the pH of the composition such that hydrolysis of the potential fragrances occur.

The compositions according to the present invention can be manufactured by techniques known in the art; and are applied in the same manner as corresponding conventional compositions (e.g., conventional liquid roll-ons, sprays, aerosols, stick products and cream products).

The total concentration of potential fragrances in the compositions according to the present invention illustratively may range from 0.05%–3% by weight, although such concentration is not limited. Also illustratively (and not limiting), the potential fragrance may represent 10%–100% of the total amount of fragrance ingredient in the composition.

As indicated previously, a plurality of potential fragrances (for example, several carbonyl acetals or ketals) preferably are compounded together in an alkaline formulation to ensure a formulation having a desirable set of "fragrances" or odors following hydrolysis, after application to the skin.

As indicated previously, the present invention, incorporating potential fragrances into compositions for contact with human skin, is particularly appropriate in connection with stick deodorant or antiperspirant products that are clear or transparent. Suitable formulations include sodium stearate-based deodorant sticks containing water, propylene glycol, monohydric alcohols, other fragrances, and color. However, the present invention is not limited to use of the potential fragrances in clear or transparent stick compositions, and also includes various compositions wherein solutions, lotions, creams and other emulsions are used as vehicles for the composition (personal care or skin care product) applied to the skin.

EXAMPLE 1

This example shows hydrolysis of various acetals or ketals of carbonyl compounds in acidic conditions, or in sweat with epidermal bacteria LT (arthrobacter species) and H6 (various of staphylococcus epidermidis), which acetals or ketals are stable under basic (alkaline) conditions. Hydrolysis of the various compounds was tested in sweat or water, as indicated.

The following four types of materials were tested for hydrolysis of the acetal or ketal:

(1) acetal in sweat or water;

(2) glucoside and ester in water;

(3) acetal and ketal by strain LT (or H6) in sweat (LT is Arthrobacter s.p., and H6 is staphylococcus epidermis); and (4) glucoside and ester with strain LT in sweat.

The procedure in connection with (1) and (2) above was as follows:

The pH of a mixture of acetal or ketal (300 μl), Nonipol 130 (Sanyo Kasei Co., Ltd.) (300 μl), Tween 80 (60 μl), and sweat (120 ml) or water (120 ml of distilled water) was regulated, and then the mixture was sterilized through a 0.45 μm micro filter. The sterilized mixture was shaken for 24 hours at 37° C. The degree of hydrolysis was then checked by gas chromatography using a dibenzyl compound as an internal standard after 3, 6, 9 and 24 hours.

The procedure in connection with (3) and (4) of the foregoing was as follows:

A mixture of acetal (or ketal) in an amount of 300 μl, Nonipol 130 (300 μl), Tween 80 (60 μl) and sweat (120 ml) was sterilized through a 0.45 μm micro filter. To the sterilized mixture, strain LT (or H6) was added, and the resultant mixture was shaken for 24 hours at 37° C. The resulting material was checked by gas chromatography using a dibenzyl as an internal standard after 3, 6, 9 and 24 hours.

The results of the foregoing experiment are shown in the following Table 1:

TABLE 1

| COMPOUND | MEDIA | PH | strain | REACTIVITY (% reacted) | | | |
|---|---|---|---|---|---|---|---|
| | | | | 3 hr | 6 hr | 9 hr | 24 hr |
| Heliotropine ethylene glycol acetal | sweat | 7.7–8.2 | — | 0 | 0 | 0 | 1.7 |
| | water | 7.2–7.9 | — | 0.4 | 3.6 | 5.6 | 11.0 |
| | sweat | 7.6–8.0 | LT | 2.2 | 4.0 | 5.9 | 12.4 |
| | sweat | 7.5–7.7 | H6 | 1.5 | 3.0 | 5.7 | 16.2 |
| | sweat | 6.2–6.4 | — | 18.1 | 32.4 | 40.7 | 64.7 |
| | water | 5.7–5.8 | — | 63.8 | 65.7 | 66.7 | 68.5 |
| Ionone dimethyl ketal | sweat | 7.6–7.8 | — | 2.4 | 19.0 | 32.8 | 25.9 |
| | water | 6.7–7.1 | — | 18.8 | 30.6 | 33.5 | 28.3 |
| | sweat | 7.4–7.6 | LT | 0.8 | 0.1 | 7.7 | 30.7 |
| | sweat | 7.3–7.7 | H6 | 18.5 | 18.1 | 16.0 | 28.8 |
| | sweat | 6.4–6.6 | — | 36.4 | 45.8 | 44.8 | 29.1 |
| | water | 6.9–7.0 | — | 13.0 | 14.8 | 28.8 | 13.8 |
| Methyl naphtyl ketone dimethyl ketal | sweat | 7.7–8.1 | — | 0.0 | 0.0 | 2.5 | 12.4 |
| | water | 7.3–8.1 | — | 0.0 | 1.2 | 6.4 | 20.0 |
| | sweat | 7.6–7.8 | LT | 0.0 | 0.3 | 3.6 | 8.8 |
| | sweat | 7.5–7.7 | H6 | 1.1 | 5.8 | 7.6 | 20.5 |
| | sweat | 6.3–6.4 | — | 26.1 | 40.2 | 50.1 | 83.3 |
| | water | 6.2–6.4 | — | 54.4 | 75.8 | 87.9 | 93.7 |
| Citral butanetriol acetal | sweat | 6.9–7.3 | — | 1.5 | 6.9 | 10.3 | 14.6 |
| | water | 8.2–9.3 | — | 0.0 | 0.1 | 0.3 | 0.3 |
| | sweat | 7.0–7.2 | LT | 4.3 | 7.5 | 12.1 | 20.8 |
| | sweat | 7.5–7.9 | H6 | 4.5 | 5.8 | 6.8 | 9.4 |
| | water | 6.6–7.0 | — | 40.8 | 66.1 | 76.8 | 46.8 |
| α-Amyl cinnamaldehyde dimethyl acetal | sweat | 7.7–8.2 | — | 1.1 | 1.3 | 4.4 | 4.4 |
| | water | 7.2–8.0 | — | 0.0 | 0.0 | 1.0 | 3.3 |
| | sweat | 7.5–7.7 | LT | 0.0 | 0.0 | 0.6 | 0.1 |
| | sweat | 7.2–7.5 | H6 | 0.0 | 0.4 | 0.5 | 0.6 |
| | sweat | 6.3–6.4 | — | 10.5 | 11.5 | 21.9 | 24.6 |
| | water | 3.5–6.2 | — | 5.9 | 12.9 | 22.1 | 36.6 |
| α-Amyl cinnamaldehyde butanetriol acetal | sweat | 7.8–8.2 | — | 3.2 | 3.4 | 3.9 | 0.6 |
| | water | 7.4–8.2 | — | 0.0 | 0.0 | 0.0 | 0.1 |
| | sweat | 7.5–7.7 | LT | 0.8 | 0.1 | 0.1 | 0.3 |
| | sweat | 6.3–6.5 | — | 2.2 | 2.3 | 0.8 | 3.4 |
| | water | 6.2–6.5 | — | 0.0 | 0.0 | 0.4 | 2.5 |
| Vanillin propyleneglycol acetal | sweat | 6.8–7.8 | — | 14.2 | 39.7 | 35.9 | 56.7 |
| | water | 7.0–7.9 | — | 10.8 | 20.3 | 22.9 | 49.5 |
| | sweat | 6.5–6.9 | — | 25.1 | 42.6 | 50.0 | 75.1 |
| | water | 6.2–6.3 | — | 20.9 | 39.2 | 48.2 | 69.8 |
| Decanal diethyl acetal | sweat | 7.3–7.9 | — | Not hydrolyzed | | | |
| | water | 7.0–7.5 | — | | | | |
| | sweat | 6.5–6.9 | — | | | | |
| | water | 6.2–6.8 | — | | | | |
| Decanal propyleneglycol acetal | sweat | 7.6–7.8 | — | Not hydrolyzed | | | |
| | water | 7.5–8.3 | — | | | | |
| | sweat | 7.5–7.7 | LT | | | | |
| C-3-Hexenyl glucoside | sweat | 7.5–7.7 | LT | Not hydrolyzed | | | |
| | water | 6.5–6.8 | | | | | |
| Phenethyl acetate | sweat | 7.5–7.7 | LT | Not hydrolyzed | | | |
| | water | 6.0–7.0 | — | | | | |
| Geranyl acetate | sweat | 7.5–7.7 | LT | Not hydrolyzed | | | |
| | water | 6.0–7.0 | — | | | | |

As can be seen in the foregoing Table 1, conjugated carbonyl compounds were hydrolyzed in acidic water or in weak acidic sweat. More reactive aromatic compounds were. hydrolyzed even in basic (alkaline) conditions (under pH=8); but in more basic (alkaline) conditions (pH=8–9), acetal or ketal compounds were not hydrolyzed.

From the foregoing, it can be seen that acetals or ketals of various carbonyl compounds are hydrolyzed to original carbonyl compounds in acidic media (pH=6–7). Acetals or ketals of carbonyl aromatic compounds (vanillin, heliotropin and methyl naphthyl ketone) are hydrolyzed even in mildly basic solutions; also, ionone dimethyl ketal and vanillin propylene glycol acetal are hydrolyzed to ionone and vanillin both in acidic and basic conditions (pH=7–8); however, acetals or ketals of certain non-conjugated carbonyl compounds, and of esters and glucoside, are not hydrolyzed to the original compounds. In addition, the strains LT and H6 cannot accelerate hydrolysis of acetal, ketal, glucoside and ester in sweat or in water.

EXAMPLE 2

The pH of a mixture of Dimethyl phenyl orthoformate (0.3 g), Nonipol 130 (0.5 g) and N-Cetane (0.1 g) as internal standard was regulated by phosphate buffer solution (50 ml), and then the mixture was shaken for 24 hours at 37° C. The degree of hydrolysis was then checked by gas chromatography after 4, 9, and 24 hours. The conditions for the gas chromatography include the following:

column: OV-10.25 mm×25 m temperature: 100°–220° (4°/min.)

The results are demonstrated as FIG. 3 and FIG. 4.

EXAMPLE 3

This example shows the results of hydrolyzing various acetals and ketals at a pH of 6. The hydrolysis procedure used is described in the following. A pH 6 phosphate buffer solution (Fisher) was prepared containing two nonionic surfactants (Igepal CO-720, 0.25% (Aldrich) and Tween 80, 0.05% (Aldrich)) to ensure solubility of the potential fragrances. To 5 ml of the pH 6 buffer was added a solution of 5 mg of the potential fragrance in 0.2 ml EtOAc and 20 μl of internal standard solution (0.6M methyl stearate in EtOAc). The solution was stirred and incubated at 37° C., and 0.5 ml aliquots were removed periodically. Each aliquot was extracted with 0.5 ml EtOAc, and 1 μl of the EtOAc layer was analyzed by gas chromatography (Hewlett Packard 5890 GC equipped with a FID and 12 m DB-5 capillary column). Quantitation of the hydrolysis was performed by monitoring the disappearance of the potential fragrance, relative to the internal standard.

The potential fragrances tested, are shown in Table 2. These potential fragrances were purchased or synthesized as described in the following.

4-Butylbenzaldehyde DEA, benzaldehyde DMA, and hydroxycitronellal DMA were obtained from Aldrich. Vanillin PGA was obtained from Pfaltz & Bauer, Inc. Amyl cinnamaldehyde DEA and DMA, anisaldehyde DEA and PGA, benzaldehyde PGA, citral DMA and PGA, decanal DEA, dodecanal DMA, heliotropin DEA, heridon, hyacinth DMA and GA (glyceryl acetal), hydratropic aldehyde DMA, isobutyl aldehyde DEA, laurinal DEA, leaf acetal, nonanal DMA, talia, and troenan were provided by Takasago International Corporation (Tokyo, Japan). All other acetals and ketals were synthesized using the general procedures below.

Diethyl acetals.

Suzaral DEA.

To a THF (500 ml) solution of suzaral (115 mM) was added triethyl orthoformate (172 mM) and a catalytic amount of p-toluenesulfonic acid monohydrate (1.15 mM). The reaction flask was equipped with a Dean-Stark trap packed with 3 Å molecular sieves and refluxed until the reaction was complete. Solvent and residual triethyl orthoformate were removed by rotary evaporation. Vacuum distillation (97° C., 400 mtorr) afforded a colorless oil (66% yield). Mass: [M]+ m/e 278. $^1$H-NMR (500 MHz, CDCl$_3$) δ0.87 (m,9H), 1.24 (m,6H), 1.84 (m,1H), 2.05 (m, 1H), 2.28 (d,2H), 2.44 (d,2H), 3.50 (t,2H), 3.69 (t,2H), 4.20 (d,2H), 7.06 (m,4H).

Dupical DEA:

Colorless oil (87% yield). MS: [M]+ 278. $^1$H-NMR: δ0.93 (m,2H), 1.04 (d,1H), 1.20 (2t,6H), (m, 1H), 1.65 (m,4H), 1.72 (t,1H), 1.85 (m,4H), 1.95 (m, 1H), 2.05 (m,3H), 2.33 (s, 1/2H), 2.65 (s, 1/2H), 3.47 (m,2H), 3.65 (m,2H), 4.47 (2t,1H) 4.95 (t, 1/2H), 5.17 (t, 1/2H).

Vanillin DEA:

Colorless oil (10% yield). MS: [M]+ 226. $^1$H-NMR: δ1.25 (t,6H), 3.55 (m,2H), 3.65 (m,2H), 3.92 (s,3H), 5.4 (s,1H), 5.4 (s,1H), 6.88 (d,1H), 6.95 (d,2H), 7.05 (s,1H).

Diethyl ketals.

Methyl naphthyl ketone DEK (diethyl ketal). To an ethanol (64 ml) solution of methyl naphthyl ketone (0.27M) was added triethyl orthoformate (0.69M). An ethanol solution of hydrochloric acid (2.4M, 1.2 ml) was added and the reaction was stirred at room temperature for 2 days. Sodium ethoxide was added to quench the acid, followed by concentration under vacuum. The acetal was filtered through carbon and celite, washed with petroleum ether, and dried under high vacuum to afford a colorless oil (90% yield). MS:[M]+ 244. $^1$H-NMR: δ1.24 (t,6H), 1.62 (s,3H), 3.47 (m,4H), 7.41 (m,2H), 7.6 (d,1H), 7.8 (m,3H), 8.05 (s,1H).

Acetyl tetralin DEK:

Colorless oil (90% yield). MS: [M]+ 248. $^1$H-NMR: δ1.22 (t,6H), 1.52 (s,3H), 1.78 (m,4H), 2.75 (m, 4H), 3.44 (m, 4H), 7.01 (d, 1H), 7.2 (m, 2H).

Alpha ionone DEK:

Colorless oil (77% yield). MS: [M]+ 266. $^1$H-NMR: δ0.8 (s,3H), 0.9 (s,3H), 1.15 (t,6H), 1.20–1.40 (m,2H), 1.38 (s,3H), 1.6 (s,3H), 2.0 (m,2H), 2.05 (d,1H), 3.45 (m,4H), 5.4 (m,2H), 5.65 (dd, 1H).

Cyclic Acetals.

Heliotropin PGA.

To a THF (300 ml) solution of heliotropin (169 mmoles) was added propylene glycol (211.3 mM) and p-toluene sulfonic acid monohydrate (1.69 mM). The reaction flask was equipped with a Dean-Stark trap packed with 3 Å molecular sieves and refluxed until complete. After concentration under reduced pressure the crude acetal was vacuum distilled (105° C., 450 millitorr), affording a colorless oil (75% yield). MS: [M]+ 208. $^1$H-NMR: δ1.34 (d, 3/2H), 1.39 (d,3/2H), 3.54 (t,1/2H), 3.60 (t, 1/2H), 4.10 (t,1/2H), 4.26 (t,1/2H), 4.34 (dt,1H), 5.72 (s,1/2H), 5.86 (s,1/2H), 5.96 (s,2H), 6.78 (d,1H), 6.96 (m,2H).

Decanal PGA:

Colorless oil (70% yield). MS:[M]+ 214. $^1$H-NMR: δ0.9 (t,3H), 1.3 (m,14H), 1.65 (m,2H), 3.4 (m, 1H), 3.9 (t,1/2H), 4.18 (m,3/2H), 4.9 (t,1/2H), 5.05 (t,1/2H).

Dodecanal PGA:

Colorless oil (68% yield). MS: [M]+ 242. $^1$H-NMR: δ0.9 (t,3H), 1.3 (m,18H), 1.65 (m,2H), 3.4 (m, 1H), 3.9 (t,1/2H), 4.18 (m,3/2H), 4.9 (t,1/2H), 5.05 (t,1/2H).

Dupical PGA:

Colorless oil (70% yield). MS:[M]+ 262. $^1$H-NMR: δ0.93 (m, 2H), 1.05 (d, 1H), 1.19 (m, 1H), 1.25 (d,3/2H), 1.30 (d,3/2H), 1.41 (m, 1H), 1.68 (m, 5H), 1.85 (m, 3H), 1.95–2.10 (m, 4H), 2.34 (s,1/2H), 2.68 (s,1/2H), 3.41 (m, 1H), 3.93 (m, 1/2H), 4.12–4.22 (m,3/2H), 4.98 (m, 1H), 4.98 (m, 1H), 5.20 (t,1/2H).

Heliotropin EGA:

Colorless oil (53% yield). MS: [M]+ 194. $^1$H-NMR: δ4.00 (m, 2H), 4.09 (m, 2H), 5.71 (s, 1H), 5.96 (s,2H), 6.79 (m, 1H), 6.96 (m,2H).

Nonanal PGA:

Colorless oil (85% yield). MS: [M]+ 200. $^1$H-NMR: δ0.87 (t,3H), 1.3 (m,12H), 1.64 (m,2H), 3.39 (m,1H), 3.93 (t,1/2H), 4.15 (m,3/2H), 4.89 (t,1/2H), 5.0 (t,1/2H).

Suzaral PGA:

Colorless oil (85% yield). MS: [M]+ 262. $^1$H-NMR: δ0.88 (m,9H), 1.26 (d,3/2H), 1.30 (d,3/2H), 1.83 (m, 1H), 2.0 (m, 1H), 2.35 (m, 1H), 2.43 (d,2H), 2.85 (m, 1H), 3.40 (m, 1H), 3.96 (m,1/2H), 4.18 (m,3/2H), 4.81 (d,1/2H), 4.89 (d,1/2H), 7.0 (m,4H).

The results of the hydrolysis are also shown in Table 2.

TABLE 2

Hydrolysis results

| Potential Fragrance | CAS Number | Hydrolysis, pH 6 |
|---|---|---|
| 4-butylbenzaldehyde diethyl acetal | 83803-80-9 | none, 24 hr |
| anisaldehyde diethyl acetal | 2403-58-9 | 100%, 1 hr |
| anisaldehyde propylene glycol acetal | 6414-32-0 | 80%, 8 hr |
| benzaldehyde dimethyl acetal | 1125-88-8 | 90%, 7 hr |
| benzaldehyde propylene glycol acetal | 2568-25-4 | none, 24 hr |
| vanillin diethyl acetal | 85377-01-1 | 99%, 0.75 hr |
| vanillin propylene glycol acetal | 68527-74-2 | 89%, 6 hr |
| heliotropin diethyl acetal | 40527-42-2 | 100%, 2 hr |
| heliotropin ethylene glycol acetal | 4405-18-9 | 64.7%, 24 hr |
| heliotropin propylene glycol acetal | 61683-99-6 | 84.8%, 48 hr |
| alpha ionone diethyl ketal | 13743-48-1 | 95.1%, 24 hr |
| beta ionone diethyl ketal | 13743-47-0 | 53.7%, 48 hr |
| beta methyl ionone diethyl ketal | not registered | 42.6%, 24 hr |
| dupical diethyl acetal | not registered | none, 45 hr |
| dupical propylene glycol acetal | not registered | none, 48 hr |
| suzaral diethyl acetal | not registered | none, 45 hr |
| suzaral propylene glycol acetal | not registered | none, 48 hr |
| amyl cinnamic aldehyde diethyl acetal | 60763-41-9 | 18%, 24 hr |
| amyl cinnamic aldehyde dimethyl acetal | 91-87-2 | 24.6%, 24 hr |
| decanal diethyl acetal | 34764-02-8 | none, 24 hr |
| decanal propylene glycol acetal | 5421-12-5 | none, 24 hr |
| dodecanal dimethyl acetal | 14620-52-1 | none, 24 hr |
| dodecanal propylene glycol acetal | 82925-11-9 | none, 48 hr |
| nonanal dimethyl acetal | 18824-63-0 | 16%, 42 hr |
| nonanal propylene glycol acetal | 68391-39-9 | none, 48 hr |
| methyl naphthyl ketone diethyl ketal | not registered | 60.1%, 48 hr |
| acetyl tetralin diethyl ketal | not registered | 91%, 48 hr |
| citral dimethyl acetal | 7549-37-3 | 90%, 2 hr |
| citral propylene glycol acetal | 10444-50-5 | 66.4%, 24 hr |
| hyacinth dimethyl acetal | 101-48-4 | none, 45 hr |
| hyacinth glyceryl acetal | 29895-73-6 | none, 45 hi |
| hydratropic aldehyde dimethyl acetal | 90-87-9 | none, 45 hr |
| hydroxycitronellal dimethyl acetal | 141-92-4 | none, 24 hr |
| laurinal diethyl acetal | 7779-94-4 | 27.8%, 45 hr |
| heridon | 181-28-2 | 51%, 24 hr |
| intreleven aldehyde diethyl acetal | not registered | none, 24 hr |
| isobutyl aldehyde diethyl acetal | 1741-41-9 | 87.1%, 45 hr |
| leaf acetal | 28069-74-1 | 55.9%, 45 hr |
| talia | 67633-92-5 | 14%, 42 hr |
| troenan | 480-24-6 | 9%, 42 hr |

The following conclusions can be drawn from these results. Acetals hydrolyze more quickly than ketals, and acyclic acetals hydrolyze more quickly than cyclic acetals. Acetals made from short-chain alcohols hydrolyze faster than acetals made from large alcohols. Dimethyl, diethyl and propylene glycol acetals generally hydrolyze quickly at a pH of 6; larger acetals will also hydrolyze, but more slowly and at a lower pH. Allylic conjugation with the hydrolysis site results in faster hydrolysis than hydrolysis of compounds with unsubstituted aryl conjugation. Electron-donating substituents on an aromatic ring in conjugation with the hydrolysis site increase the rate of hydrolysis; and electron-withdrawing groups at the beta position of an olefin conjugated to the hydrolysis site decrease the rate of hydrolysis.

In the following are set forth examples of potential fragrances incorporated in various products, according to the present invention. In the following examples, conventional methods of emulsification, gelation, co-solvency and mixing are used. The methods of forming the compositions are well known in the art. In many cases, especially when heating is required during processing, it is desirable to add the fragrances (regular or potential) last, to reduce fragrance loss due to volatilization or decomposition.

Example A.
Water Based Gelled Deodorant Sticks

| | % W/W | | | | | |
|---|---|---|---|---|---|---|
| | 1 | 2 | 3 | 4 | 5 | 6 |
| Sodium Stearate | 7.0 | 6.5 | 7.0 | — | 1.0 | 6.5 |
| DBMSA | — | — | — | 1.5 | 1.5 | — |
| Magnesium Oxide | — | — | — | — | — | 10.0 |
| Water | 25.8 | 23.1 | 25.0 | 23.5 | 26.0 | 13.1 |
| Ethanol | — | — | — | — | — | 10.0 |
| Propylene glycol | 66.0 | 69.0 | 45.0 | 30.0 | 40.0 | 59.0 |
| Dipropylene glycol | — | — | 19.5 | 31.2 | 21.2 | — |
| Sorbitol | — | — | — | 3.5 | 3.5 | — |
| M-pyrol | — | — | — | 5.0 | 4.0 | — |
| Dimethicone copolyol | — | — | — | 4.0 | — | — |
| Triclosan° | 0.2 | 0.2 | — | 0.3 | 0.3 | 0.2 |
| PPG-3-Myristyl ether°° | — | — | 2.0 | — | 1.0 | — |
| Potential Fragrance* | 0.5 | 1.2 | 1.0 | 1.0 | 1.0 | 1.2 |
| Regular Fragrance** | 0.5 | — | 0.5 | — | 0.5 | — |
| | 100.0 | 100.0 | 100.0 | 100.0 | 100.0 | 100.0 |

°Vendor: Ciba Geigy
°°Vendor: Croda Synthetic Chemicals Ltd.
*May be one or more potential fragrance ingredients
**Fragrance of prior art - not a potential fragrance The procedure is known to those skilled in the art. It is desirable to add the fragrances last.

Example B.
Non-aqueous Gelled Deodorant Sticks

| | % W/W | |
|---|---|---|
| | 1 | 2 |
| Stearyl Alcohol | 21.0 | 16.0 |
| Castorwax MP-70 | — | 4.0 |
| PPG-15-stearyl ether | — | 3.0 |
| Glyceryl Monostearate | 0.5 | 0.5 |
| PEG-100 | 0.5 | 0.5 |
| Cyclomethicone | 60.5 | 57.5 |
| Magnesium Oxide | 15.0 | — |
| Sodium bicarbonate | — | 16.0 |
| Potential fragrance | 2.5 | 1.5 |
| Regular fragrance | — | 1.0 |
| | 100.0 | 100.0 |

Procedure:
Melt the stearyl alcohol and castorwax at 70–80° C. While stirring, add the glyceryl monostearate, PEG-100 and PPG-15 stearyl ether. While cooling, add the cyclomethicone and maintain at 55–60° C. Add the magnesium oxide or sodium bicarbonate. While stirring add the fragrances last and cool.

| Example C. Water-based Roll-on Deodorants | | | | |
|---|---|---|---|---|
| | % W/W | | | |
| | 1 | 2 | 3 | 4 |
| Water | 44 | 45 | 73 | 78.0 |
| Cyclomethicone | 33 | 30 | — | — |
| Magnesium Oxide | 15 | — | 15 | 5.0 |
| Sodium bicarbonate | — | 15 | — | — |
| Sodium silicate | — | — | — | 5.0 |
| Dimethicone copolyol° (10% active) | 5 | 6 | — | — |
| Polysorbate 20°° | 1 | 2 | — | — |
| PPG-15 Stearyl ether | — | — | 5.0 | 5.0 |
| Steareth-2°°° | — | — | 1.5 | 1.5 |
| Steareth-78°°°° | — | — | 3.5 | 3.5 |
| Potential Fragrance | 1.5 | 1.0 | 2.0 | 2.0 |
| Regular Fragrance | 0.5 | 1.0 | — | — |
| | 100.0 | 100.0 | 100.0 | 100.0 |

°Vendor: Dow Corning Ltd.
°°Vendor: Emery Industries Inc.
°°°Vendor: Brooks & Perkin Inc.
°°°°Vendor: Brooks & Perkin Inc.

| Example D. Suspension Deodorant Roll-Ons | | |
|---|---|---|
| | % W/W | |
| | 1 | 2 |
| Cyclomethicone | 66.5 | 74.0 |
| Bentone | 2.5 | 2.5 |
| SD-40 Alcohol | 1.0 | 1.0 |
| Magnesium Oxide | 18.0 | — |
| Sodium bicarbonate | — | 15.0 |
| Dimethicone | 10.0 | — |
| Isopropyl myristate | — | 5.0 |
| Potential fragrance | 2.0 | 1.5 |
| Regular fragrance | — | 1.5 |
| | 100.0 | 100.0 |

| Example E. Powder Compositions | | | | |
|---|---|---|---|---|
| | % W/W | | | |
| | 1 | 2 | 3 | 4 |
| Talc | 89.0 | 73.0 | 81.0 | 56.0 |
| Cornstarch | — | 15.0 | — | 30.0 |
| Magnesium Oxide | 5.0 | — | — | — |
| Sodium bicarbonate | — | 10.0 | — | 4.0 |
| Calcium silicate | — | — | 2.0 | — |
| Oatmeal | 2.0 | — | 15.0 | 5.0 |
| Potential fragrance | 2.0 | 1.0 | 1.5 | 3.0 |
| Regular fragrance | 1.0 | 1.0 | 0.5 | — |
| Dimethicone | 1.0 | — | — | 2.0 |
| | 100.0 | 100.0 | 100.0 | 100.00 |

| Example F. Baby Lotions | | | |
|---|---|---|---|
| | % W/W | | |
| | 1 | 2 | 3 |
| Oil Phase | | | |
| Glyceryl stearate | 1.5 | 1.0 | 0.7 |
| Isopropyl palmitate | 1.5 | 1.0 | 1.3 |
| Lauramine° | 0.5 | 0.5 | 0.5 |
| Mineral oil | 1.5 | 1.0 | 1.0 |
| Stearic Acid | 0.8 | 0.8 | 1.0 |
| Cetyl Alcohol | 0.7 | 0.8 | 0.7 |
| Propyl paraben | 0.1 | 0.1 | 0.1 |
| Potential fragrance | 1.3 | 1.0 | 1.5 |
| Regular fragrance | 0.3 | 0.5 | — |
| Water Phase | | | |
| Propylene glycol | 2.0 | 2.0 | 2.0 |
| Carbomer 934 | — | 0.1 | — |
| Trimethamine | 1.0 | 0.8 | 1.2 |
| Tetrasodium EDTA | 0.5 | 0.5 | 0.6 |
| Sodium hydroxide | q.s. to pH = 8.2 | — | q.s. pH = 8.5 |
| Triethanol-amine | — | q.s. to pH = 8.0 | 0.5 |
| Water | q.s. to 100.0 | q.s. to 100.0 | q.s. to 100.0 |

°Vendor: Akzo NV NL

Procedure:
Heat water to 70° C. Add other water phase ingredients, adding the triethanolamine and/or sodium hydroxide last. Separately melt the contents of the oil phase together, then add the oil phase to the water phase with agitation. Cool to set point and fill.

| Example G. Skin or Body Creams | | |
|---|---|---|
| | % W/W | |
| | 1 | 2 |
| Oil Phase | | |
| Glyceryl Stearate | 5.0 | 5.5 |
| Isopropyl Myristate | 3.0 | 3.5 |
| Stearic Acid | 2.5 | 2.0 |
| Propyl paraben | 0.1 | 0.1 |
| Potential fragrance | 1.5 | 0.7 |
| Regular fragrance | — | 0.7 |
| Water Phase | | |
| Glycerine | 6.0 | 6.0 |
| Triethanalamine | 1.0 | 1.0 |
| Methyl paraben | 0.2 | 0.2 |
| Tetrasodium EDTA | 0.5 | — |
| Magnesium Oxide | 3.0 | 3.5 |
| Water | q.s. to 100.0 | q.s. to 100.0 |

Procedure similar to Baby Lotions

Example H.
Ointments

| | % W/W | | |
|---|---|---|---|
| | 1 | 2 | 3 |
| Zinc Oxide | 20.0 | 25.0 | 12.0 |
| Magnesium Oxide | — | — | 8.0 |
| Mineral Oil | 15.0 | — | 12.0 |
| White Ointment | 63.0 | — | 61.5 |
| White Petrolatum | — | 50.0 | — |
| Starch | — | 23.0 | 5.0 |
| Potential fragrance | 2.0 | 1.0 | 1.0 |
| Regular fragrance | — | 1.0 | 0.5 |
| | 100.0 | 100.0 | 100.0 |

Example I.
After-Shave Lotions and Colognes

| | % W/W | |
|---|---|---|
| | 1 | 2 |
| Propylene glycol | 2.0 | 2.0 |
| Ethanol | 75.0 | 80.0 |
| Water | 16.5 | 9.3 |
| Sodium bicarbonate | 2.0 | 2.0 |
| Sodium hydroxide | 0.2 | — |
| Tetrasodium EDTA | 0.5 | 0.5 |
| Benzophenone - 4° | 0.3 | 0.2 |
| Potential fragrance | 2.0 | 2.0 |
| Regular fragrance | 1.5 | 4.0 |
| | 100.0 | 100.0 |

°Vendor: BASF AG

Example J.
Aerosol Deodorant Compositions

| | 1 | 2 |
|---|---|---|
| Benzethonium chloride | 0.21 | — |
| Dipropylene glycol | 1.00 | — |
| SDA-40 Alcohol (anhydrous) | 65.00 | 0.75 |
| Potential fragrance | 1.50 | 1.50 |
| Regular fragrance | 0.50 | — |
| Hydrocarbon A-46 propellant | — | 74.00 |
| Hydrocarbon A-70 propellant | 31.40 | — |
| Trimethamine | 0.39 | — |
| Cyclomethicone | — | 12.00 |
| Isopropyl myristate | — | 4.00 |
| Magnesium oxide | — | 7.00 |
| Bentone 38 | — | 0.75 |
| | 100.0 | 100.00 |

Example K.
Shaving Creams

| | % w/w |
|---|---|
| Stearic Acid | 8.5 |
| Triethanolamine | 3.0 |
| Potassium hydroxide | 1.0 |
| Polysorbate 20 | 1.2 |
| Glycerin | 2.2 |
| Lauramide DEA | 0.8 |
| Isopropyl myristate | 0.5 |

Example K.
Shaving Creams

| | % w/w |
|---|---|
| Water | 79.3 |
| A-46 Propellant | 3.5 |
| | 100.0 |

Accordingly, by the present invention, a composition, e.g., for application to the skin, containing a potential fragrance (that is, body activated fragrance, which under alkaline conditions has little or no odor but which releases a fragrance compound by hydrolysis, under acidic conditions, e.g., on the skin), achieves a delayed release of fragrance. By incorporating such potential fragrance in a sodium stearate-based deodorant or antiperspirant stick product, a transparent or clear deodorant or antiperspirant stick product can be achieved.

While we have shown and described several embodiments in accordance with the present invention, it is understood that the same is not limited thereto, but is susceptible to numerous changes and modifications as are known to one having ordinary skill in the art, and we therefore do not wish to be limited to the details shown and described herein, but intend to cover all such modifications as are encompassed by the scope of the appended claims.

We claim:

1. A composition for application to the skin, the composition being capable of producing an alkaline pH when in contact with water and including (1) a vehicle such that when the composition is in contact with water, the composition is at the alkaline pH, and (2) at least one potential fragrance, the at least one potential fragrance being at least one compound having a first level of aroma in the composition, and reacting when in contact with the skin to respectively produce a compound having a fragrance, the fragrance being of a second level of aroma, the second level being stronger than the first level, wherein the at least one potential fragrance is selected from the group consisting of heliotropine ethylene glycol acetal, ionone dialkyl ketal, methyl naphthyl ketone dialkyl ketal, citral polyol acetal, α-amyl cinnamaldehyde dialkyl acetal, α-amyl cinnamaldehyde polyol acetal, vanillin dialkyl acetal, vanillin alkylene acetal, anisic aldehyde dialkyl acetal, anisic aldehyde polyol acetal, citral dialkyl acetal, and vanillin polyol acetal.

2. The composition according to claim 1, wherein said at least one potential fragrance does not undergo hydrolysis at a pH level greater than 7.5 and undergoes hydrolysis at a pH of 7.5 or less.

3. The composition according to claim 1, wherein said at least one potential fragrance includes a plurality of potential fragrances, each being a compound selected from said group, the plurality of potential fragrances providing, in combination, after said reacting, compounds producing a combination fragrance.

4. The composition according to claim 1, wherein the ionone dialkyl ketal is ionone dimethyl ketal or ionone diethyl ketal; the methyl naphthyl ketone dialkyl ketal is methyl naphthyl ketone dimethyl ketal or methyl naphthyl ketone diethyl ketal; the citral polyol acetal is selected from the group consisting of citral ethylene glycol acetal, citral butanediol acetal, citral butanetriol acetal and citral propylene glycol acetal; the α-amyl cinnamaldehyde dialkyl acetal is α-amyl cinnamaldehyde dimethyl acetal or α-amyl cinnamaldehyde diethyl acetal; the α-amyl cinnamaldehyde polyol acetal is selected from the group consisting of α-amyl cinnamaldehyde propylene glycol acetal, α-amyl cinnamaldehyde butanetriol acetal and α-amyl cinnamaldehyde ethylene glycol acetal; the vanillin dialkyl acetal is vanillin dimethyl acetal or vanillin diethyl acetal; the vanillin alkylene acetal is vanillin ethylene acetal or vanillin propylene acetal; the anisic aldehyde dialkyl acetal is anisic aldehyde dimethyl acetal or anisic aldehyde diethyl acetal; the anisic aldehyde polyol acetal is selected from the group consisting of anisic aldehyde propylene glycol acetal, anisic aldehyde butanetriol acetal and anisic aldehyde ethylene glycol acetal; and the citral dialkyl acetal is citral dimethyl acetal or citral diethyl acetal; and the vanillin polyol acetal is vanillin propylene glycol acetal.

5. The composition according to claim 1, wherein said at least one potential fragrance is included in the composition in an amount of 0.05% to 3% by weight of the total weight of the composition.

6. The composition according to claim 1, wherein the at least one potential fragrance is included in the composition in an amount of 10% to 100% by weight of the total amount of fragrance components in the composition.

7. The composition according to claim 1, wherein said vehicle is a vehicle for forming a liquid roll-on composition, whereby the composition can be applied to the skin as a roll-on.

8. The composition according to claim 1, wherein said vehicle is a vehicle for forming a stick deodorant composition, whereby the composition can be applied to the skin as a stick product.

9. The composition according to claim 8, wherein the stick deodorant composition is a transparent composition containing said at least one potential fragrance.

10. The composition according to claim 9, wherein the stick deodorant composition includes, as said vehicle, sodium stearate as a gelling agent, whereby the transparent stick deodorant composition is a sodium stearate based stick deodorant.

11. The composition according to claim 10, wherein the stick deodorant composition further includes water, propylene glycol and monohydric alcohols.

12. The composition according to claim 1, wherein the vehicle is a powder, whereby the composition can be applied to the skin as a powder.

13. The composition according to claim 1, wherein said vehicle is a vehicle for forming a baby lotion, wherein the composition is a baby lotion.

14. The composition according to claim 1, wherein said vehicle is a vehicle for forming an after-shave lotion, whereby the composition is an after-shave lotion.

15. The composition according to claim 1, wherein the composition includes water.

16. A composition for imparting a fragrance, the composition being capable of producing an alkaline pH when in contact with water and including (1) a vehicle such that when the composition is in contact with water, the composition is at an alkaline pH, and (2) at least one potential fragrance, the at least one potential fragrance being at least one compound having a first level of aroma in the composition at the alkaline pH, but reacting in a more acidic environment than the alkaline pH to produce a compound having a fragrance, the fragrance being of a second level of aroma that is stronger than the first level, wherein the at least one potential fragrance is selected from the group consisting of heliotropine ethylene glycol acetal, ionone dialkyl ketal, methyl naphthyl ketone dialkyl ketal, citral polyol acetal, α-amyl cinnamaldehyde dialkyl acetal, α-amyl cinnamaldehyde polyol acetal, vanillin dialkyl acetal, vanillin alkylene acetal, anisic aldehyde dialkyl acetal, anisic aldehyde polyol acetal, citral dialkyl acetal, and vanillin polyol acetal.

17. The composition according to claim 16, wherein the composition has a pH greater than 8.0 when in contact with water, and wherein the at least one potential fragrance is at least one compound that is hydrolyzed at a pH of at most 8.0 to produce the compound having the fragrance of the second level of aroma.

18. A method of providing a fragrance, comprising the steps of:
(a) applying a fragrancing composition, the fragrancing composition being capable of producing an alkaline composition when in contact with water and including (1) a vehicle such that when the composition is in contact with water, the composition is at an alkaline pH, and (2) at least one potential fragrance, the at least one potential fragrance being at least one compound having a first level of aroma in the alkaline composition, prior to application, and producing at least one compound with a fragrance, the fragrance being of a second level of aroma, stronger than the first level, when in a more acidic environment than the alkaline pH, wherein the at least one potential fragrance is selected from the group consisting of heliotropine ethylene glycol acetal, ionone dialkyl ketal, methyl naphthyl ketone dialkyl ketal, citral polyol acetal, α-amyl cinnamaldehyde dialkyl acetal, α-amyl cinnamaldehyde polyol acetal, vanillin dialkyl acetal, vanillin alkylene acetal, anisic aldehyde dialkyl acetal, anisic aldehyde polyol acetal, citral dialkyl acetal, and vanillin polyol acetal; and
(b) lowering the pH of an environment of the at least one potential fragrance, after application, so as to produce said at least one compound with the fragrance, of the second level of aroma.

19. The method according to claim 18, wherein the fragrancing composition is applied to skin of a human, and wherein the pH of the environment is lowered by the natural buffering capacity of the skin to maintain a skin surface pH of 5.5–7.0.

20. The method according to claim 19, wherein the fragrancing composition is a stick deodorant, the stick deodorant being applied to the skin in the axillary region.

21. A composition for application to the skin, the composition being capable of producing an alkaline pH when in contact with water and including (1) a vehicle such that when the composition is in contact with water, the composition is at the alkaline pH, and (2) at least one potential fragrance, the at least one potential fragrance being at least one compound having a first level of aroma in the composition, and reacting when in contact with the skin to respectively produce a compound having a fragrance, the fragrance being of a second level of aroma, the second level being stronger than the first level, wherein the at least one potential fragrance is selected from the group consisting of anisaldehyde diethyl acetal, anisaldehyde propylene glycol acetal, benzaldehyde dimethyl acetal, vanillin diethyl acetal, vanillin propylene glycol acetal, heliotropin diethyl acetal, heliotropin ethylene glycol acetal, alpha ionone diethyl ketal, beta ionone diethyl ketal, beta methyl ionone diethyl ketal, amyl cinnamic aldehyde diethyl acetal, amyl cinnamic aldehyde dimethyl acetal, nonanal dimethyl acetal, methyl naphthyl ketone diethyl ketal, acetyl tetralin diethyl ketal, citral dimethyl acetal, citral propylene glycol acetal, laurinal diethyl acetal, heridon, isobutyl aldehyde diethyl acetal, leaf acetal, talia and troenan.

22. The composition according to claim 21, wherein said at least one potential fragrance does not undergo hydrolysis at a pH level greater than 7.5 and undergoes hydrolysis at a pH of 7.5 or less.

23. The composition according to claim 21, wherein said at least one potential fragrance includes a plurality of potential fragrances, each being a compound selected from said group, the plurality of potential fragrances providing, in combination, after said reacting, compounds producing a combination fragrance.

24. The composition according to claim 21, wherein said at least one potential fragrance is included in the composition in an amount of 0.05% to 3% by weight of the total weight of the composition.

25. The composition according to claim 21, wherein the at least one potential fragrance is included in the composition in an amount of 10% to 100% by weight of the total amount of fragrance components in the composition.

26. The composition according to claim 21, wherein said vehicle is a vehicle for forming a liquid roll-on composition, whereby the composition can be applied to the skin as a roll-on.

27. The composition according to claim 21, wherein said vehicle is a vehicle for forming a stick deodorant composition, whereby the composition can be applied to the skin as a stick product.

28. The composition according to claim 21, wherein the vehicle is a powder, whereby the composition can be applied to the skin as a powder.

29. The composition according to claim 21, wherein said vehicle is a vehicle for forming a baby lotion, whereby the composition is a baby lotion.

30. The composition according to claim 21, wherein said vehicle is a vehicle for forming an after-shave lotion, whereby the composition is an after-shave lotion.

31. The composition according to claim 21, wherein the composition includes water.

32. A composition for imparting a fragrance, the composition being capable of producing an alkaline pH when in contact with water and including (1) a vehicle such that when the composition is in contact with water, the composition is at an alkaline pH, and (2) at least one potential fragrance, the at least one potential fragrance being at least one compound having a first level of aroma in the composition at the alkaline pH, but reacting in a more acidic environment than the alkaline pH to produce a compound having a fragrance, the fragrance being of a second level of aroma that is stronger than the first level, wherein the at least one potential fragrance is selected from the group consisting of anisaldehyde diethyl acetal, anisaldehyde propylene glycol acetal, benzaldehyde dimethyl acetal, vanillin diethyl acetal, vanillin propylene glycol acetal, heliotropin diethyl acetal, heliotropin ethylene glycol acetal, alpha ionone diethyl ketal, beta ionone diethyl ketal, beta methyl ionone diethyl ketal, amyl cinnamic aldehyde diethyl acetal, amyl cinnamic aldehyde dimethyl acetal, nonanal dimethyl acetal, methyl naphthyl ketone diethyl ketal, acetyl tetralin diethyl ketal, citral dimethyl acetal, citral propylene glycol acetal, laurinal diethyl acetal, heridon, isobutyl aldehyde diethyl acetal, leaf acetal, talia and troenan.

33. The composition according to claim 32, wherein the composition has a pH greater than 8.0 when in contact with water, and wherein the at least one potential fragrance is at least one compound that is hydrolyzed at a pH of at most 8.0 to produce the compound having the fragrance of the second level of aroma.

34. A method of providing a fragrance, comprising the steps of:

(a) applying a fragrancing composition, the fragrancing composition being capable of producing an alkaline composition when in contact with water and including (1) a vehicle such that when the composition is in contact with water, the composition is at an alkaline pH, and (2) at least one potential fragrance, the at least one potential fragrance being at least one compound having a first level of aroma in the alkaline composition, prior to application, and producing at least one compound with a fragrance, the fragrance being of a second level of aroma, stronger than the first level, when in a more acidic environment than the alkaline pH, wherein the at least one potential fragrance is selected from the group consisting of anisaldehyde diethyl acetal, anisaldehyde propylene glycol acetal, benzaldehyde dimethyl acetal, vanillin diethyl acetal, vanillin propylene glycol acetal, heliotropin diethyl acetal, heliotropin ethylene glycol acetal, alpha ionone diethyl ketal, beta ionone diethyl ketal, beta methyl ionone diethyl ketal, amyl cinnamic aldehyde diethyl acetal, amyl cinnamic aldehyde dimethyl acetal, nonanal dimethyl acetal, methyl naphthyl ketone diethyl ketal, acetyl tetralin diethyl ketal, citral dimethyl acetal, citral propylene glycol acetal, laurinal diethyl acetal, heridon, isobutyl aldehyde diethyl acetal, leaf acetal, talia and troenan; and (b) lowering the pH of an environment of the at least one potential fragrance, after application, so as to produce said at least one compound with the fragrance, of the second level of aroma.

35. The method according to claim 34, wherein the fragrancing composition is applied to skin of a human, and wherein the pH of the environment is lowered by the natural buffering capacity of the skin to maintain a skin surface pH of 5.5–7.0.

* * * * *